(12) United States Patent
Monsan et al.

(10) Patent No.: US 7,846,874 B2
(45) Date of Patent: Dec. 7, 2010

(54) METHOD FOR THE IDENTIFICATION OF A METABOLIC PATHWAY FAMILY BY MEANS OF POSITIVE SELECTION

(75) Inventors: Pierre Monsan, Mondonville (FR); Claude Bensoussan, Renneville (FR); Philippe Reulet, Paris (FR); Renaud Nalin, Auzielle (FR); Patrick Robe, Odars (FR); Karine Tuphile, Morsang sur Orge (FR); Benjamin Gillet, Lyons (FR); Pierre Pujic, Serezin du Rhône (FR)

(73) Assignee: Libragen, Toulouse (FR)

( * ) Notice: Subject to any disclaimer, the term of this patent is extended or adjusted under 35 U.S.C. 154(b) by 216 days.

(21) Appl. No.: 10/591,087

(22) PCT Filed: Mar. 22, 2005

(86) PCT No.: PCT/FR2005/000696

§ 371 (c)(1),
(2), (4) Date: Aug. 29, 2006

(87) PCT Pub. No.: WO2005/095634

PCT Pub. Date: Oct. 13, 2005

(65) Prior Publication Data

US 2007/0184449 A1    Aug. 9, 2007

(30) Foreign Application Priority Data

Mar. 23, 2004  (FR) .................................. 04 02985

(51) Int. Cl.
*C40B 30/04* (2006.01)
*C40B 20/04* (2006.01)

(52) U.S. Cl. ......................... 506/10; 435/390; 435/383; 435/373; 506/7

(58) Field of Classification Search ................... 506/10, 506/7; 435/390, 383, 373
See application file for complete search history.

(56) References Cited

U.S. PATENT DOCUMENTS

| 6,368,793 | B1 | 4/2002 | Hoch et al. |
| 6,379,964 | B1* | 4/2002 | del Cardayre et al. ....... 435/440 |
| 6,391,640 | B1* | 5/2002 | Minshull et al. ............ 435/440 |
| 7,008,767 | B2* | 3/2006 | Handelsman et al. .......... 435/6 |
| 2003/0068807 | A1* | 4/2003 | Hoch et al. .............. 435/235.1 |
| 2006/0063244 | A1* | 3/2006 | Schultz et al. .............. 435/183 |

FOREIGN PATENT DOCUMENTS

WO    WO 98/17811 A    4/1998

OTHER PUBLICATIONS

Rondon, M. R. et al. "Cloning the Soil Metagenome: A Strategy for Accessing the Genetic and Functional Diversity of Uncultured Microorganism", *Applied and Environmental Microbiology*, Jun. 2000, pp. 2541-2547, vol. 66, No. 6.

* cited by examiner

*Primary Examiner*—Teresa D. Wessendorf
(74) *Attorney, Agent, or Firm*—Saliwanchik, Lloyd & Saliwanchik (57) ABSTRACT

The invention relates to the direct selection of metabolic pathways having a determined function in the transformation of a substrate {Ai} into a target product {B}, which is of interest in the industrial, pharmaceutical or agri-food sectors. More specifically, the invention relates to the detection, within metagenomic libraries, of novel biosynthesis pathways involved in a biochemical reaction having a known product {B}. The selection and characterization of said novel metabolic pathways enables {B} to be produced enzymatically. The invention provides an alternative to the chemical synthesis of the molecule in question {B}. Moreover, and above all, the invention can be used specifically to target and exploit the only metabolic pathways enabling the transformation of {Ai} into {B}, while eliminating the associated metabolic pathways that can catabolise the target product {B}.

8 Claims, 5 Drawing Sheets

Figure 1: General diagram of the process for detecting metabolic pathways

Figure 2: Diagram of the primary transformation-selection cycle A) process, B) Phenotypes identified Figure 3: Diagram of the secondary transformation-selection cycle A) process, B) Phenotypes identified Figure 4: Diagram of the alternative transformation-selection cycle Apra, Apramycine; Apra$^{R/S}$, Resistance/sensitivity to apramycine; Cat, Chloramphenicol; Cat$^{R/S}$, Resistance/sensitivity to chloramphenicol Figure 5: Alternative transformation-selection process

METHOD FOR THE IDENTIFICATION OF A METABOLIC PATHWAY FAMILY BY MEANS OF POSITIVE SELECTION

CROSS-REFERENCE TO RELATED APPLICATION

This application is the U.S. national stage application of International Patent Application No. PCT/FR2005/000696, filed Mar. 22, 2005, the disclosure of which is hereby incorporated by reference in its entirety, including all figures, tables and amino acid or nucleic acid sequences.

FIELD OF THE INVENTION

The invention relates to the direct selection of metabolic pathways having a determined function in the transformation of a substrate {A} into a target product {B}, which is of interest in the industrial, chemical, pharmaceutical, cosmetic, agrochemical or nutraceutical field. More specifically, the invention relates to the detection, within metagenomic libraries, of novel biosynthesis pathways involved in a biochemical reaction which leads to the product {B}. By the selection and characterisation of said novel metabolic pathways enabling {B} to be produced enzymatically, the invention both provides an alternative to the chemical synthesis of the molecule in question {B}, and enables the synthesis of product {B} which up till now was inaccessible chemically.

BACKGROUND OF THE INVENTION

Biocatalysis, defined as the biological synthesis of the molecules in question enzymatically, has been becoming more popular by offering a strong alternative to chemical synthesis, in terms of cost, time, purification steps, and simplicity of use. The introduction of any new biocatalysis process on an industrial scale necessitates, however, (i) identifying the enzyme (or the enzymes) which make(s) it possible to specifically convert the substrate provided into the desired product, (ii) identifying the enzyme (or the enzymes) which make(s) it possible to implement the catalysis in a stable manner and in the particular conditions linked to the industrial process (thermostability, pH, or tolerance to denaturation conditions of organic solvents).

Due to their universal distribution, including in the most extreme environments, microorganisms are known for being able to perform totally original enzymatic functions and in conditions compatible with the industrial processes mentioned above.

However, the promising approach of exploiting these bacterial functions has always been considerably limited by a technological obstacle: the isolation and in vitro culture of the enormous potential offered by the bacterial diversity. Most bacteria developing in complex natural environments (soils and sediments, aquatic environments, digestive systems) have not been cultivated because their optimal culturing conditions are unknown or too difficult to reproduce. Numerous scientific works demonstrate this established fact, and it is now widely admitted that only between 0.1 and 1% of the bacterial diversity, including all environments, have been isolated and cultivated (Amann et al, 1995, Microb. Rev., 59: 143-169). Even if the search for novel biocatalytic pathways within collections of microbic strains has proved to be effective, it nevertheless has the major disadvantage of only exploiting a tiny part of the bacterial biodiversity.

New approaches have been developed in order to overcome this critical point of isolating bacteria in order to gain access to this enormous genetic potential offered by the adaptation systems of bacteria developed over their long evolution. This approach is called Metagenomics because it relates to a set of genomes from a bacterial community without any distinction (metagenome).

Metagenomics involves the direct extraction of DNA from environmental samples, their propagation and their expression in cultivatable bacterial hosts. Metagenomics in the strict sense was first of all used for identifying new bacterial phyla (Pace, 1997, Science, 276: 734-740). This approach is based upon the specific cloning of genes recognised for their phylogenetic interest, such as for example DNAr 16S. Other developments have been implemented in order to identify new enzymes of environmental or industrial interest (Terragen Diversity Patent No. U.S. Pat. No. 6,441,148). In these two approaches, metagenomics starts with a selection of the desired genes. This selection is made by a PCR (Polymerase Chain Reaction) approach, generally before the cloning step. In the latter case, the cloning vector is preferably an expression vector (i.e. it contains regulating sequences upstream of the cloned fragment of DNA, enabling it to express the cloned DNA in a give expression host).

More recent developments consider the metagenome as a whole. Thus, no selection and no identification is made before the metagenomic DNA library is created, in a totally random fashion. This approach therefore gives access to the whole genetic potential of the bacterial community being explored without any a priori.

In general, bacteria play an important role in the function of ecosystems. In fact, they are well represented quantitatively. For example, it is estimated that one gram of soil can contain between 1 000 and 10 000 different species of bacteria with between $10^7$ and $10^9$ cells, considering cultivatable and non-cultivatable bacteria. Reproducing this whole diversity in metagenomic DNA libraries requires the ability to generate and manage a large number of clones.

In this latter approach, the DNA libraries are made up of several dozen, hundreds of thousands, or even several million recombinant clones which differ from one another by the DNA which they have incorporated. For this, the average size of the cloned metagenomic inserts is of the utmost importance in the search for bacterial biosynthesis pathways because most of the time these pathways are organised in clusters in the bacteria. The larger the cloned fragments of DNA (larger than 30 Kb), the more the number of clones to be analysed is limited and the greater the possibility of reproducing complete metabolic pathways which make it possible to obtain the conversion of a substrate {A} into a target product {B} and into a source of growth.

Given the large number of recombinant clones to be studied and the number of trials to be carried out, numerous laboratories are tending to use high density hybridisation systems (high density membranes or DNA chips), in particular for the characterisation of bacterial communities (for a review, see Zhou et al., 2003, Curr. Opin. Microbial., 6: 288-294).

Even if none of these data relate to metagenomic libraries, they nevertheless provide a great deal of information such as the quantification of different functional genes (Cho et al., 2003), the study of functional genes and their diversity (Wu et al., 2001, Appl. Environ. Microbiol., 67: 5780-5790) and the direct detection of DNAr 16S genes (Small et al., 2001). Just one study relates to the use of metagenomics in combination with DNA chips (Sebat et al., 2003, Appl. Environ. Microbiol., 69: 4927-4934) for the identification of clones containing DNA which has come from non-cultivatable bacteria and their selection for additional analysis.

The screening of enzymatic activities or of antibacterial activities from metagenomic libraries has been widely described in the scientific literature. The studies have related, for example, to the direct detection of chitinase (Cottrell et al., 1999, Appl. Environ. Microbiol., 65: 2553-2557), lipase (Henne et al., 2000, Appl. Environ. Microbiol., 66: 3113-3116), DNA, and amylase (Rondon et al., 2000, Appl. Environ. Microbiol., 66: 2541-2547) activity. In these studies, the host bacteria containing the recombinant clones are placed in culture on a medium complemented by the substrate of which metabolisation is sought, and the screening of the activity is generally based upon the appearance of haloes or precipitates around the colonies, or by a change to the appearance of the colonies which are metabolising the substrate being studied. It should be noted that the enzymatic activities detected by means of these examples are new activities for the host bacterium, but are not essential for the growth of the latter in the examples provided. A similar approach was described in the patent (Chromaxome No. 5,783,431). This patent describes a method of screening activity based upon the encapsulation of individual or pooled clones from a library in a stable, inert and porous matrix (advantageously alginate), in the form of macro- or micro-droplets. The droplets are for example subjected to a liquid culture containing the nutritive elements necessary for bacterial growth and a substrate (for example X-glucosaminide, X-acetate, X-glucopyranoside) the metabolisation of which is expressed by the appearance of blue colouring.

Alternatively, the phenotypical screening described in the Proteus Patent (N° FR 2 786 788) is based upon a prior preparation of the nucleic acid sequences encoding the target protein (upstream and downstream elements necessary for the transcription and translation of the target genes), the in vivo transcription and translation, and then the detection and measurement of the activity of the target proteins.

All of these screening methods require the use of high throughput systems because they involve subjecting all of the clones to the screening test in order to identify the clones in question which respond positively to the tests. For this purpose, the company Diversa, leader in the domain of the discovery of new molecules, has developed a unique platform, called the GigaMatrix, enabling ultra-high throughput screening, of around 1 billion clones per day See Worldwide Website: diversa.com/techplat/gigamatrix/default.asp).

Another approach has already been described in patent WO 00/22170 of Microgenomics (U.S. Pat. No. 6,368,793 B1). This patent describes a methodology for identifying a metabolic pathway transforming a substrate S into a desired product T by creating or identifying a genetically manipulated organism of which the capability of implementing this reaction is placed under the control of an inducible promoter. This organism is used for screening fragments of nucleic acids in order to detect a gene involved in the transformation of a substrate into a product. The implementation of this method requires the identification and genetic characterisation of the genes responsible for the degradation of T in the expression host so that they can be placed under the control of an inducible promoter. This type of construct cannot always be considered, in particular when the genes in question are spread over the genome and there is a possible risk of "leaking" into the inducer. On the other hand, it represents extremely hard work which has to be repeated for every study of a product T. Finally, in this approach, the organism used must be capable of incorporating and metabolising S and T. All of the elements mentioned demonstrate the limits of the efficacy of this type of approach.

The majority of these technologies, with the exception of that described by Microgenomics, therefore require the prior organisation of libraries, i.e. the individualisation, storage and preservation of the clones in formats compatible with the screening systems mentioned above. Moreover, the adequacy of a metagenomic library for a given problem (for example the search for a specific enzymatic function) can only be established when all of the clones making up this library have been subjected to the screening. Several hundreds of thousands of clones must often be screened in order maybe to detect just one clone of interest. The creation of a metagenomic library is in fact subject to a certain number of limitations, such as the prior choice of the environment being explored, the bacterial community (or communities) being considered within this environment, the cloning or expression vector, the sizes of the cloned inserts, and the host organism likely to best express the heterological metagenomic DNA.

The time required and the means used to create the metagenomic library and then its screening is therefore key, with small hope of success. An increase in the chances of discovery would involve, absolutely, the creation of a metagenomic library specific to each problem, in order to best respond to the objectives set.

SUMMARY OF THE INVENTION

Figure 1:
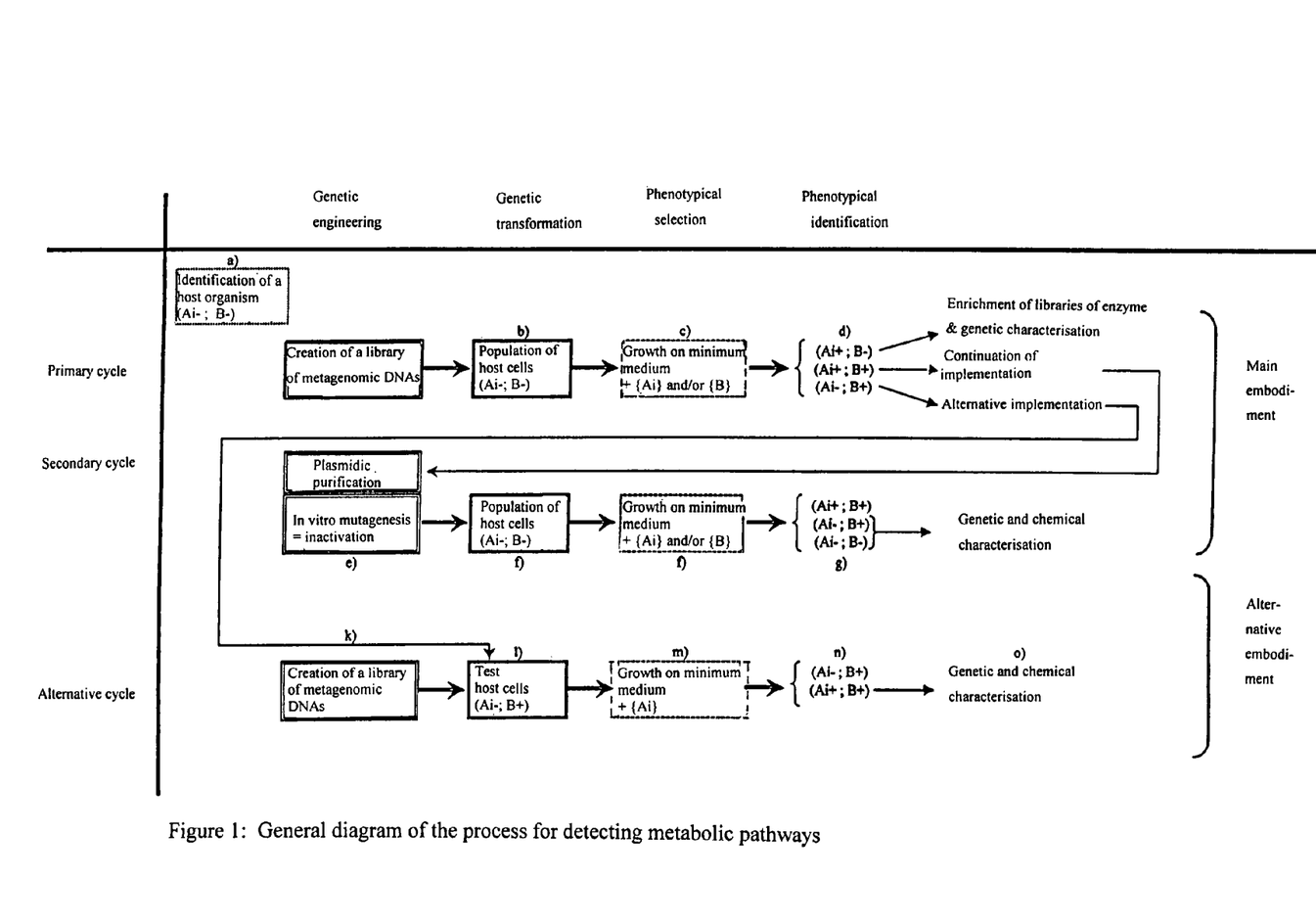
FIG. 1: General diagram of the process for detecting metabolic pathways.

This invention relates to a method for the identification of a metabolic pathway or of metabolic pathway families enabling the transformation of one or more substrate(s) $\{Ai\}$ into a desired product $\{B\}$. This method is based upon the selection or the preparation of cells including at least one metabolic pathway or a metabolic pathway family enabling the transformation of one or more substrates $\{Ai\}$ into a desired product $\{B\}$. Furthermore, it enables the identification and characterisation of the gene or genes encoding the enzyme or the enzymes involved in the conversion of the substrate $\{Ai\}$ into product $\{B\}$. This invention, based upon a series of transformation-selection-purification cycles, targets the enormous microbic potential (FIG. 1). This method includes the following steps:

a) providing a population of host cells (Ai−; B−) incapable of metabolising said substrate or substrates $\{Ai\}$ and said product $\{B\}$;

b) transforming said population of host cells with a library of nucleic acid sequences;

c) testing in parallel said population of host cells transformed on minimum media containing either one of the substrates $\{Ai\}$, or said product $\{B\}$ as the only source of an element essential to growth; and, d) selecting said transformed host cell or cells capable of growth on a minimum medium containing one of the substrates $\{Ai\}$ and on a minimum medium containing said product $\{B\}$ (Ai+; B+), then optionally isolating the nucleic acid molecule introduced at the time of the transformation in step b) and giving the phenotype (Ai+; B+).

Preferably, the method includes, before step c), a step consisting of testing the population of transformed host cells on a minimum medium containing the substrate(s) $\{Ai\}$ and said product $\{B\}$ as the only source of an element essential to growth and selecting said transformed host cell or cells capable of growth on said minimum medium containing the substrate(s) $\{Ai\}$ and said product $\{B\}$; said selected host cell(s) then being subjected to step c) and the subsequent steps.

The method according to this invention can also include, after step d), the following steps:

e) implementing in vitro mutagenesis, or any other method known by the man skilled in the art which leads to the same result, of the nucleic acid molecule isolated from said host cell or cells (Ai+; B+) transformed in step d);

f) re-transforming the population of host cells (Ai−; B−) described in step a) with the population of nucleic acids mutated in vitro in step e) and testing the host cell(s) thus transformed on minimum media containing either one of the substrates {Ai}, or said product {B} as the only source of an element essential to growth; and, g) selecting said transformed host cell(s) incapable of growth on a minimum medium containing one of the substrates {Ai} and capable of growth on a minimum medium containing said product {B} (Ai−; B+), then optionally isolating the mutated nucleic acid molecule.

In addition, the method can include the characterisation of the gene or genes encoding the enzyme or enzymes involved in the conversion of the substrate {Ai} into product {B} and isolated from said transformed host cell(s) (Ai−; B+) selected in step g).

In a first alternative, the method includes, after step f), instead of or parallel to step g):

h) selecting said transformed host cell(s) which has (have) become incapable of growing on a minimum medium containing one of the substrates {Ai} and on a minimum medium containing said product {B} (Ai−; B−);

i) carrying out a quantitative analysis of the accumulation of the product {B} of said transformed host cell(s) (Ai−; B−) on a rich medium supplemented with {Ai}; and j) selecting said transformed host cell(s) (Ai−; B−) accumulating the product {B} on a rich medium and optionally isolating in parallel the mutated nucleic acid molecule introduced during the transformation of step f).

In addition, the method can include the characterisation of the gene or genes encoding the enzyme or enzymes involved in the conversion of the substrate {Ai} into product {B} isolated from said transformed host cell(s) (Ai−; B−) selected in step j).

In a second alternative, the method includes, after step c), instead of or in parallel to step d) and the subsequent steps, the following steps:

k) selecting said transformed host cell(s), incapable of growth on a minimum medium containing one of the substrates {Ai} and capable of growth on a minimum medium containing said product {B}, called receiving cells (Ai−; B+);

l) transforming said receiving cell(s) (Ai−; B+) with a library of sequences of nucleic acid;

m) testing in parallel said transformed receiving cell(s) (Ai−; B+) on a minimum medium containing one of the substrates {Ai};

n) selecting said transformed receiving cell(s) capable of growth on a minimum medium containing one of the substrates {Ai}; and o) characterising the gene or genes encoding the enzyme or enzymes involved in the conversion of the substrate {Ai} into product {B} and isolated from said transformed receiving cell(s) (Ai+; B+) selected in step n).

Said library of sequences used in step m) can be the same as that used in step b) or be a distinct library. If said sequence library is (i) the same as that used in step b), i.e. the selection marker (resistance to an antibiotic, or auxotrophy marker) is the same as that present in the receiver cell(s) of phenotype (Ai−; B+), or (ii) different from that used in step b) but nevertheless relates to the same selection marker, then it is necessary to modify the selection marker for the nucleic acid sequence giving the phenotype (Ai−; B+), as described in steps kk) to kkkkk). Said modification, advantageously based upon the replacement of the initial resistance to an antibiotic by a resistance to a second antibiotic, will make it possible to apply to step m) a double selection pressure making it possible to select the transformed cells containing the two nucleic acid sequences: the nucleic acid sequence present initially and giving the capability to grow on {B} and the nucleic acid sequence newly acquired and giving the capability to convert {Ai} into {B}.

Preferably, the method includes, before step m), testing said host cell(s) (Ai−; B+) transformed on a minimum medium containing several substrates {Ai} as the only source of an element essential to growth and selecting said host cell(s) capable of growth on said minimum medium containing several substrates {Ai}; said selected host cell(s) then being subjected to step m) and the subsequent steps.

In this second alternative, the invention also relates to a method in which:

between steps k) and l), said host cell(s) (Ai−; B+) is/are modified by the replacement of the first selection marker present in the vector containing the nucleic acid sequence introduced in step b) by a new selection marker;

said library of nucleic acid sequences from step l) includes a different selection marker to that carried by said host cell(s) (Ai−; B+)

the method further includes the following steps:

kk) the extraction and purification of the vectors contained in said host cell(s) selected in step k);

kkk) the in vitro mutagenesis of said vector purified in step kk), advantageously by transposition with a transposable element carrying for example a functional resistance to an antibiotic different from that already existing on this vector.

kkkk) the transformation of said host cell(s) (Ai−; B−) incapable of metabolising said substrate or substrates {Ai} and said product {B} by the mutated nucleic acids obtained in the previous step;

kkkkk) the selection of the transformed host cells containing just said second selection marker; these transformed cells, of phenotype (Ai−; B+), formally called receiving cells, are then the object of the transformation described in step l).

Said host cells are eukaryotic or prokaryotic cells. Preferably, they are:

cultivatable in standard conditions known by the man skilled in the art, transformable or competent and capable of stably maintaining the transforming exogenous DNA.

In one preferred embodiment, said host cells are bacteria.

Said library of nucleic acid sequences can be a metagenomic library. In a first embodiment, said library of nucleic acid sequences comes from cultivatable prokaryotic or eukaryotic organisms. In a second embodiment, said library of nucleic acid sequences comes from non-cultivatable prokaryotic or eukaryotic organisms.

In one preferred embodiment of the invention, the element essential to growth is carbon.

Preferably, the selection marker is a resistance gene to an antibiotic.

The invention also relates to host cells selected by the methods according to this invention, and to their use, in particular in bio-processes using these host cells capable of transforming one or more substrates {Ai} into a desired product {B}. More specifically, this invention relates to the use of a host cell selected in step g), j) or n) of the methods according to this invention in a process for preparing the product {B} from the substrate {Ai}.

The invention also relates to the gene or genes encoding the enzyme or enzymes involved in the conversion of the substrate {Ai} into product {B} identified by the methods of this invention, a vector containing it or them, a transformed cell containing it or them, as well as any use of the latter. More specifically, this invention relates to the use of a transformed host cell with the gene or genes encoding the enzyme or enzymes involved in the conversion of the substrate {Ai} into product {B} characterised according to any of the methods according to this invention in a process for preparing the product {B} from the substrate {Ai}.

Finally, this invention relates to a method for the identification, selection, or preparation of a host cell (Ai–; B–) incapable of metabolising said substrate or substrates {Ai} and said product {B} including the following steps:

testing a population of host cells, cultivatable in standard laboratory conditions and in industrial production conditions, transformable, and capable of stably maintaining the transforming exogenous DNA, on a minimum medium containing the substrate(s) {Ai} and said product {B} as the only source of an element essential to growth; and, selecting the host cell(s) incapable of growth on said minimum medium containing the substrate(s) {Ai} and said product {B}.

The host cell can be a prokaryotic or eukaryotic cell, preferably a bacterium.

The invention also relates to a host cell cultivatable in standard conditions known by the man skilled in the art, transformable or competent, capable of stably maintaining the exogenous transforming DNA, and incapable of growth on said minimum medium containing the substrate(s) {Ai} and said product {B} as the only source of an element essential to growth, in particular a host cell obtained by the process indicated above. Furthermore, it relates to the use of this type of host cell for the identification of at least one metabolic pathway or metabolic pathway family enabling the transformation of one or more substrate(s) {Ai} into a desired product {B}.

i is a whole number between 1 and n, more specifically between 1 and 100, and preferably between 1 and 50 or 1 and 10.

DETAILED DESCRIPTION OF THE INVENTION

This invention proposes selecting and identifying a metabolic pathway enabling the transformation of a substrate {Ai} into a product {B}, not dependent upon the creation/identification of an organism capable of metabolising {B} under an inducible signal into an essential component and not dependent either upon the capability of incorporating the desired product {B}. The invention makes it possible to specifically exploit metabolic pathways originating from organisms capable of producing the target {B} but also capable of catabolising it. In fact, because the invention specifically exploits the metabolic pathways making it possible to convert a substrate {Ai} into a product {B}, it makes it possible to eliminate all of the associated catabolism pathways of the product {B} capable of affecting the accumulation of {B} in the original organism.

The invention proposes considerably reducing the time and the costs associated with the search for a new enzymatic function within metagenomic libraries, making the desired function directly detectable by positive selection. Preferably, the desired function is essential to the survival of the recombined cell. Detection of this metabolic pathway, leading non-exclusively to the transformation of a substrate {Ai} into a target product {B}, therefore involves the compound {B} being, directly or indirectly, strictly required for the growth of the host cell. The invention is distinguishable de facto from a complementation search process which would aim to detect the metabolic pathways enabling the host cell to grow on {Ai}.

In a first embodiment the process of the invention includes a primary selection-transformation cycle (FIG. 2) including the following steps:

A—The identification of a host strain, preferably bacterial, incapable of developing on one (or more) substrate(s) {Ai} (i between 1 and n) and on the product {B} of the desired function;

B—The transformation of said strain identified by a library of nucleic acid sequences, preferably environmental DNA, cloned in an appropriate vector;

C—The primary selection of recombinant clones on a minimum medium containing the substrate(s) {Ai} and the target product {B} as the only sources of an element essential to growth (FIG. 1). The recombinant clones capable of metabolising at least one of the precursors provided (one or more substrates {Ai} and/or the target product {B}) are preserved, then tested in parallel on minimum medium containing just one of the precursors. This primary selection therefore makes it possible to select in one step three types of phenotype:

type 1: recombinant clones capable of growing both on a (or several) substrate(s) {Ai} and on the target product {B}. These clones of phenotype (Ai+; B+) are likely to convert {Ai} into {B} and so are therefore subjected to the following step;

type 2: recombinant clones capable of growing only on a (or several) substrate(s) {Ai} but not on the target product {B}. These clones of phenotype (Ai+; B–) are a priori incapable of producing the target product {B}; and, type 3: recombinant clones capable of growing only on the target product {B}. These clones of phenotype (Ai–; B+) can advantageously enable the development of a receiving strain of the host organism useable for detecting by direct selection any recombinant clone capable of synthesising the target product {B}. These clones can be used in an alternative transformation-selection embodiment described below.

Figure 2:
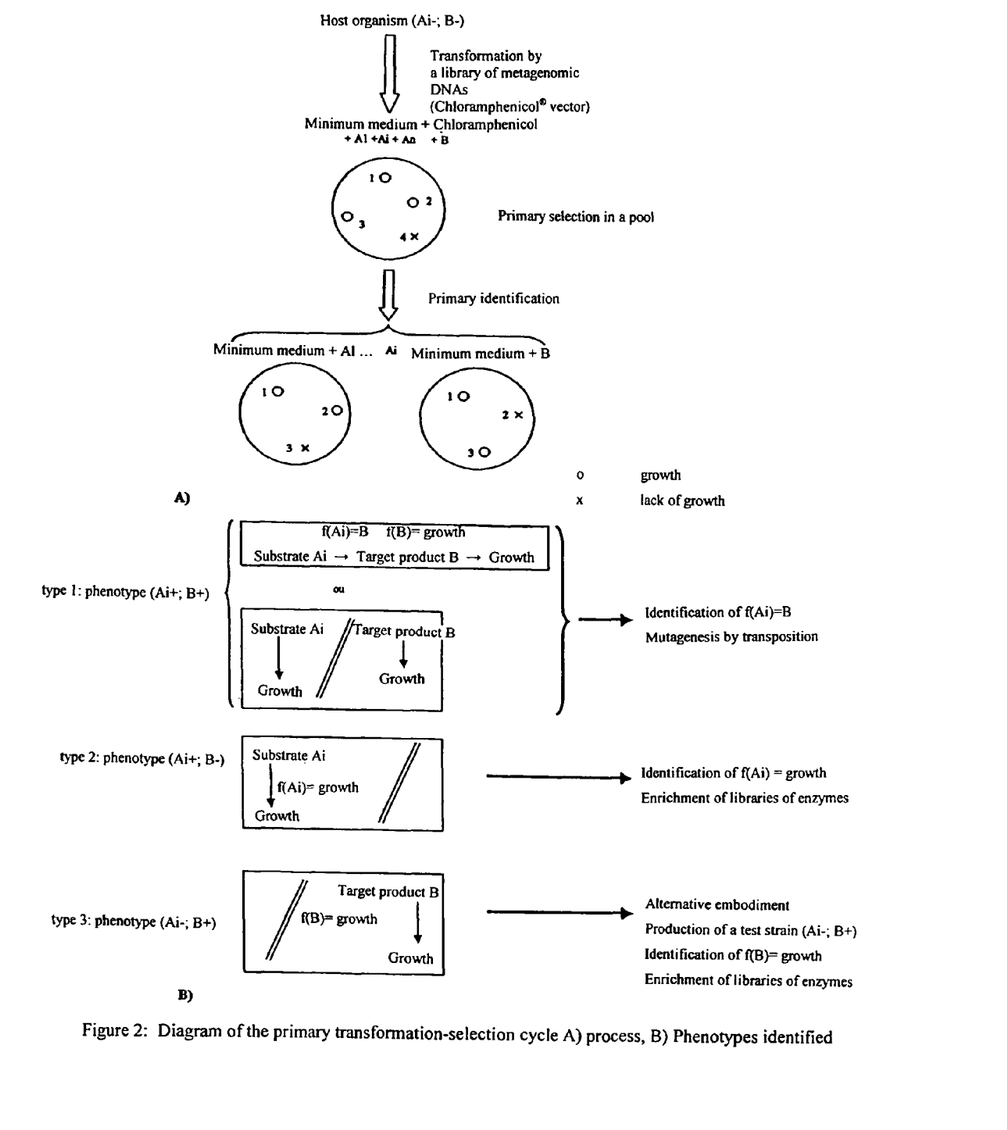
FIG. 2: Diagram of the primary transformation-selection cycle.

The capability of growing on {Ai} and {B} can be associated or be independent (cf FIG. 2).

D—The in vitro mutagenesis of the nucleic acids from the transforming sequence library and isolated from the clones with a phenotype (Ai+; B+).

Figure 3:
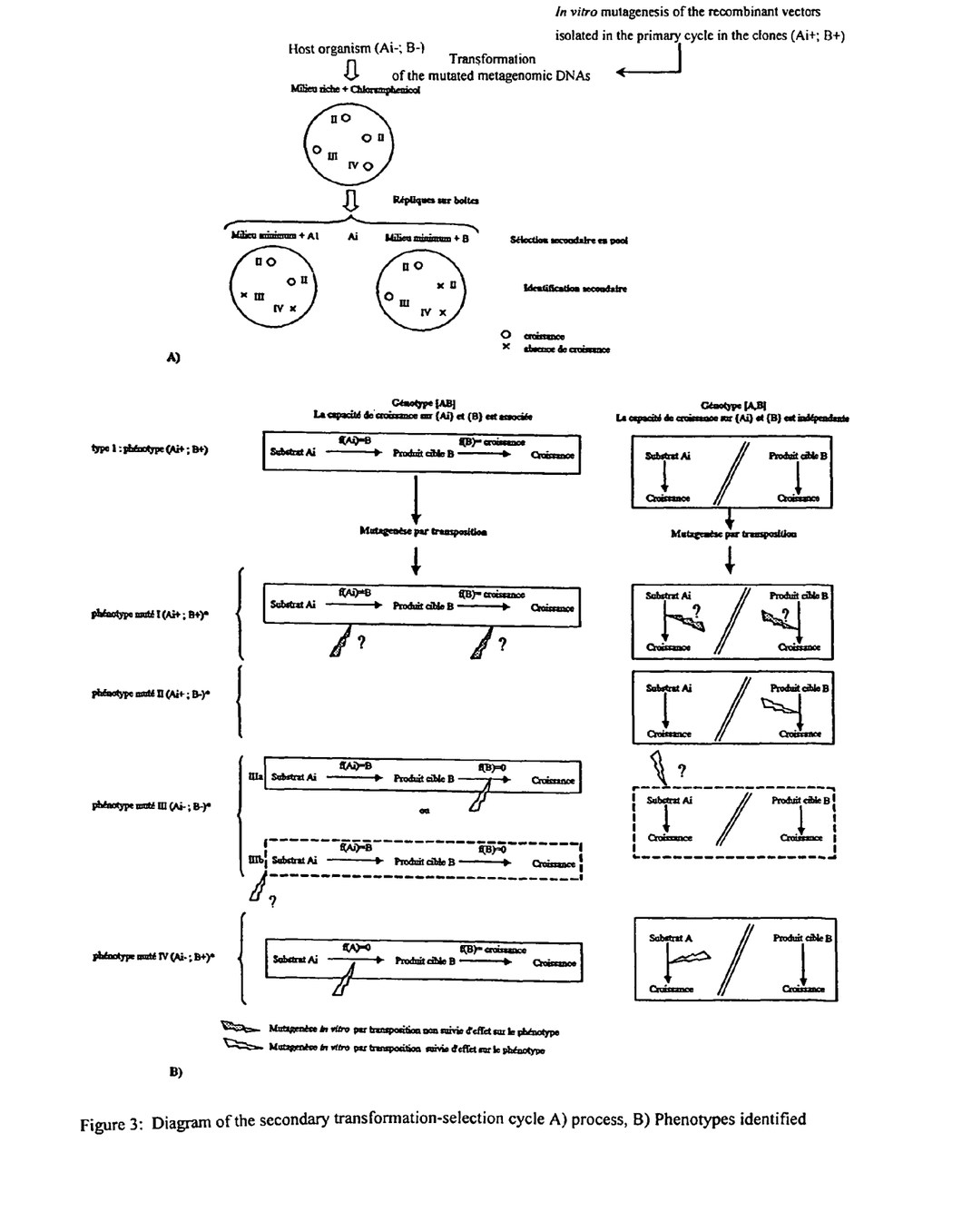
FIG. 3: Diagram of the secondary transformation-selection cycle.

E—The parallel selection on {Ai} and on {B} of the clones resulting from the transformation by the mutated nucleic acids, enables the identification of the transformed clones affected by the mutagenesis (FIG. 3). This selection makes it possible to select:

transformed clones resulting from mutation, of phenotype (Ai−; B−), having lost the capability of growing on {Ai} and on {B }. This change of phenotype can be explained either because (i) the metabolic pathway of {Ai} passes via {B} and the metabolism of {B} is disrupted (mutated phenotype IIIa), or because (ii) the mutagenesis has reached an element common to {Ai} and {B} such as for example a regulation element, a common transporter (phenotype IIIb).

F—The quantitative analysis of {Ai} and {B} by direct or indirect analytical methods, by means of phenotypes (Ai−; B−).

G—The genetic characterisation of the biocatalyst (function: {Ai} is converted into {B}) by means of the phenotypes (Ai−; B+) or the phenotypes (Ai−; B−) accumulating the product {B} on a rich medium supplemented with {Ai}).

Only phenotypes (Ai−; B+) and (Ai−; B−) of the transforming clones produced by in vitro mutagenesis enable the identification and characterisation of the novel metabolic pathways sought transforming {Ai} into {B}. The accumulation of {B} and its chemical detection is implemented by culturing the phenotypes (Ai+; B+), or preferably (Ai−; B−), on a rich medium supplemented with {Ai}.

An advantage of the process of the invention is only considering in this type of primary selection the positive clones because only these clones have the capability of developing. Thus, it is not necessary to screen all of the clones contained in the library.

In an alternative embodiment of the invention, when the primary selection step of the first embodiment does not make it possible to detect clones having a phenotype (Ai+; B+), any (Ai−; B+) phenotypes offer the possibility of developing a receiving strain of phenotype (Ai−; B+) capable of being co-transformed by a second metagenomic library. This alternative embodiment makes it possible to exploit within the metagenomic library the clones (Ai+; B−) capable of converting at least one of the substrates {Ai} into target product {B} but incapable of metabolising {B} (clones not selected in the primary selection step of the first embodiment).

Based upon a transformation-selection system, the invention:

makes it possible to directly select metabolic pathways converting a (or several) perfectly characterised substrate(s) into a target product of interest;

makes it possible to directly select, in parallel, perfectly characterised metabolic pathways metabolising a (or several) substrate(s) as (a) single source(s) of an essential element. Following genetic and chemical characterisation, these metabolic pathways make it possible to enrich specialist enzyme libraries;

makes it possible in an alternative way to easily develop a receiving strain of the host organism, capable of growing on a target product of interest, and useable de facto for a second transformation-selection cycle for the conversion of a or several perfectly characterised substrate(s) into this target product of interest. This receiving strain of the host organism is characterised in that its development results from the temporary integration of a recombinant vector and that its own genetic patrimony remains unchanged.

makes it possible to exploit, during each transformation-selection cycle, the enormous genetic potential of metagenomic libraries to great effect, without it being necessary to structure in advance these libraries and, defacto, without it being necessary to resort to high throughput screening systems.

The lack of prior structuring of the libraries consequently makes it possible to shift one's efforts into creating metagenomic libraries which optimise the chances of discovering the target metabolic pathway.

The invention further relates to the selection of a host cell incapable of metabolising a substrate {Ai} and incapable of metabolising a desired product {B}. Preferably, this host cell is a bacterial host. These are, non-restrictively, *E. coli, Bacillus, Streptomyces, Pseudomonas*, and *Nocardia, Acinetobacter*. This cell must have the capability of being transformable by any of the techniques known by the man skilled in the art. This can be, non-restrictively, transformation by electroporation, by conjugation, by transduction, or by infection. This cell is used as an expression host for individualising the vectorised fragments of DNA.

Definitions

Metagenome means all of the genomes of a microbic community of a given environment.

Metagenomics means, in the strict sense of the term, the global analysis of a metagenome independently of any artificial culture of the microorganisms. It is commonly accepted, beyond the direct study of the genetic information (metagenomic DNA), that metagenomics is based upon the prior creation of metagenomic libraries.

Metagenomic DNA library means a population of metagenomic DNAs cloned in a cloning or expression vector, enabling the transfer and maintenance of this metagenomic DNA in a (or several) host organism(s). The metagenomic library can be non-redundant, in that each cloned metagenomic molecule of DNA is unique, or can be amplified, in that each cloned metagenomic molecule of DNA has been multiplied.

Metagenomic library means a population of clones from a host organism having incorporated the population of cloned metagenomic DNAs, as referred to above (recombinant clones). The metagenomic library can be non-redundant in that every recombinant clone is unique, or can be amplified, in that every recombinant clone has been multiplied. The amplification of an original non-redundant library thus enables the division of the amplified library into sub-libraries, within which the diversity remains representative both of that of the amplified library and of that of the original non-redundant library.

Recombinant vector means an expression or cloning vector having integrated with exogenous genetic information, for example genomic DNA or metagenomic DNA.

Recombinant clone means a population of identical clonal cells of a host organism having integrated a recombinant vector, for example by genetic transformation.

Biocatalytic pathway means a set of catalytic proteins (enzymes) implementing the conversion of a starting compound (substrate) into a final compound (target product).

Metabolic pathway family means a set of nucleic acid sequences, the expression product of which is capable of implementing the transformation of a substrate {A} into a product {B}.

Shuttle vector means a vector enabling the transfer and the maintenance of genetic information from one (or more) donor bacterial species or strain(s) to one or more host organism(s) or strain(s) or species.

Description of the Environments

The invention is first of all based upon the creation of metagenomic libraries originating from an environmental sample. Soil and sediments form major environments for the search for novel active metabolites, not only due to the very large quantity of microorganisms that they contain, but also due to the considerable diversity of these microorganisms. Microorganisms have been detected in a very great number of environments, ranging from the stratosphere to abyssal depths, including extreme habitats in terms of the physicochemical conditions which prevail there. The invention applies non-restrictively to samples taken from soil, sediments, aquatic environments (fresh or sea water), plants, insects, animals, bioreactors such as biofilms, fermenters and activated sludge, but also from animal- or human-derived environments (such as for example rumen, faeces), and advantageously all environments having a quantitative (strong concentration of microorganisms) or qualitative (specificity of the microbic community or communities) advantage.

The environmental sample contains a multitude of organisms including eubacteria, archaebacteria, algae, fungi, yeasts, protozoans, viruses, phages, or parasites. The microorganisms can be represented by extremophiles such as thermophiles, psychrophiles, acidophiles, halophiles, etc. The environmental sample can contain cultivatable or non-cultivatable, known or unknown microorganisms, as well as free nucleic acids and organic matter.

Preparation of the Nucleic Acids

The environmental DNA is collected from cultivatable or non-cultivatable organisms by any of the techniques known by the man skilled in the art. Two main approaches are generally adopted in order to extract environmental DNA. The first approach, called the direct approach, consists of extracting the nucleic acids from the sample by means of in situ lysis of the microorganisms, followed by extensive purification of the released nucleic acids. The lysis of the bacterial cells can be implemented by the single or combined use of multiple processes for physically, chemically and/or enzymatically disrupting the cell walls and membranes, processes known by the man skilled in the art (for a review, see Robe et al., 2003, Eur. J. Soil Biol., 39 :183-190). The extensive purification of the nucleic acids released during the lysis can be implemented, individually or in combination, by numerous methods known by the man skilled in the art, including, non-restrictively, ultracentrifugation on cesium chloride gradients, passing over hydroxyapatite columns, electrophoresis on agarose gel, filtration on resins, or any other commercialised process for the purification of nucleic acids (for a review, see Robe et al., 2003). The second approach, called the indirect approach, consists of a prior separation of the microorganisms of the sample, non-restrictively, by differential centrifugation or by centrifugation on density gradients, followed by lysis of the microorganisms separated in this way, then extensive purification of the released nucleic acids. The steps of lysis of the microorganisms and purification of the nucleic acids are all implemented by using, individually or combined, numerous methods known by the man skilled in the art and mentioned above.

The relative efficacy of these two approaches as well as their respective advantages and disadvantages have been the object of numerous scientific studies, and are known by the man skilled in the art. Establishing the strategy for extracting the nucleic acids, i.e. the choice of one or other of these two approaches and the choice of the different methods, is based non-restrictively upon the characteristics of the environment being examined, upon the targeted microorganisms (all or some of the microorganisms of this environment) and their characteristics, upon the size of the nucleic acids, and upon the choice of the cloning vector and the cloning strategy chosen.

Host Organisms

Any vector-host system known in the prior art can be used in this invention. The identification of a host cell forms Step 1 of this invention. The host cell can be eukaryotic or prokaryotic. Preferably, the host cell used is a bacterial host. These can be, non-restrictively, *Escherichia coli, Bacillus subtilis, Streptomyces lividans, Pseudomonas,* or *Nocardia, Acinetobacter.* Examples of eukaryotic host cells, without being restricted to these, are yeasts and fungi. The host cell (i) can originate from collections of public strains, from private laboratories or commercial companies ; (ii) must be selected or modified for its inability to metabolise the substrate(s) {Ai} and the target product {B}; (iii) must be able to be cultivated in the standard conditions known by the man skilled in the art; (iv) must be capable of being transformed by any of the techniques known by the man skilled in the art ; (v) must finally stably maintain the transforming exogenous DNA despite possible systems such as recombination, restriction.

Cloning and Expression Vectors

The nucleic acids are cloned within an appropriate expression vector, maintenance of the DNA being replicatable. The expression vector used depends upon the size of the purified nucleic acids, the desired size of the insert in fine (generally between 5 kb and over 100 kb), and upon the expression host chosen which is preferably a bacterial host.

Numerous cloning or expression vectors have been described in the prior art. Non-restrictively, these are plasmids, cosmids such as those marketed by the companies Stratagene (SuperCos and pWE15) and Epicentre Technologies (pWeb cosmid cloning kit), fosmids as described by Kim et al. (1992, Nucl. Acids Res. 20: 1083-1085), artificial chromosomes PAC as described by Ioannou et al., (1994, Nat. Genet., 6: 84-89), artificial chromosomes BAC as described by Shizuya et al. (1992, Proc. Natl. Acad. Sci., 89: 8794-8797), artificial chromosomes YAC as described by Larin et al. (1991, Proc. Natl. Acad. Sci., 88: 4123-4132), phagemids and vectors derived from phages such as those marketed by the company Stratagene (Lambda Dash II and Zap II), viral vectors. Preferably, the vectors are of the cosmid, fosmid, BAC, YAC and P1-derivative type because they enable the cloning of large fragments of DNA (between 30 kb and 200 kb and over for the BACs and the YACs). The vectors can either be integrative in that they integrate randomly or in a controlled way into the genome of the host cell, or preferably be replicative in that the vector is maintained in the host cell independently of the genome of this cell. By definition, the cloning vectors contain a certain number of elements necessary for maintaining the vector in the host cell (origin of functional replication), or else necessary for the selection and/or the detection of the vector in this cell (marker gene such as for example a resistance gene to an antibiotic under the functional promoter in the host cell and enabling a positive selection pressure). Due to the specificity of these constitutive elements, the vectors have a wider or narrower host spectrum.

Cloning

The cloning process, i.e. the introduction of the sequences of nucleic acid, preferably purified metagenomic DNAs, into the appropriate vector, requires numerous steps of molecular manipulation of the DNAs (in a non-limitative way for the restrictions, dephosphorylations, ligations) which have been widely described, for example in Current Protocols in Molecular Biology, Eds. F. M. Ausubel, R. Brent, R. E. Kingston, D. D. Moore, J. G. Seidman, J. A. Smith and K. Struhi, published by Greene Publishing Associates and Wiley Inter-Science. Two approaches for creating metagenomic libraries can be considered.

In a first preferred embodiment, the metagenomic library is formed directly in a shuttle vector specific of one or more hosts, preferably bacterial, for example as described in patents N° WO 01/40497A2 (Aventis Pharma, 1999) and WO 99/67374 (Biosearch Italia, 1999) for *Streptomyces*. In a second embodiment, the purified nucleic acids are cloned in a general vector, for example of the fosmid or BAC type, then the recombinant vectors are modified, individually or in a pool, advantageously by transposition as described in patent application No. PCT/EP 03/07765 (Libragen). In this process, the transposition makes it possible to introduce, either into the vector, or into the insert (disruption or activation), the genetic elements necessary for the transfer, the replication or the integration of the recombinant vector in the chosen host cell, preferably a bacterial host. This post-modification of the clones of the library can be implemented individually (metagenomic library structured in the format of 96 or 384 microplaques) or collectively (non-structured metagenomic library). The transformation of the population of host cells identified in step 1) by a population of cloned DNAs forms Step 2 of this invention. In the two embodiments, the metagenomic library can be structured in advance in that all of the clones of the library are individualised in a format capable of being automated (96, 384, 1536 microplaques) or preferably be preserved in the form of a mixture of recombinant clones. In this preferred preservation mode, the library can advantageously be amplified in that the host cells, after transformation or infection, are multiplied over a specific number of cycles, leading to every recombinant clone of the library being represented by n copies in the amplified library, and the amplified library being able to be subjected to numerous simultaneous screening or selection tests, without any loss of diversity.

Detection and Identification of the Metabolic Pathways

Step 3: The recombinant clones are directly selected, without a prior culture step, on a minimum culture medium containing both n substrates Ai (i between 1 and n) and the target product {B} as the only sources of an essential element, as well as an antibiotic (such as chloramphenicol) making it possible to maintain a selection pressure on the host cells having integrated a recombinant vector. This primary selection step, relating to an original or amplified library of several dozen or even several hundreds of thousands of clones, makes it possible to consider in fine just the recombinant clones capable of metabolising one of the substrates {Ai} independently of the target product {B}, or the target product {B}, or one of the substrates {Ai} by means of {B}. This step is optional however.

Figure 4:
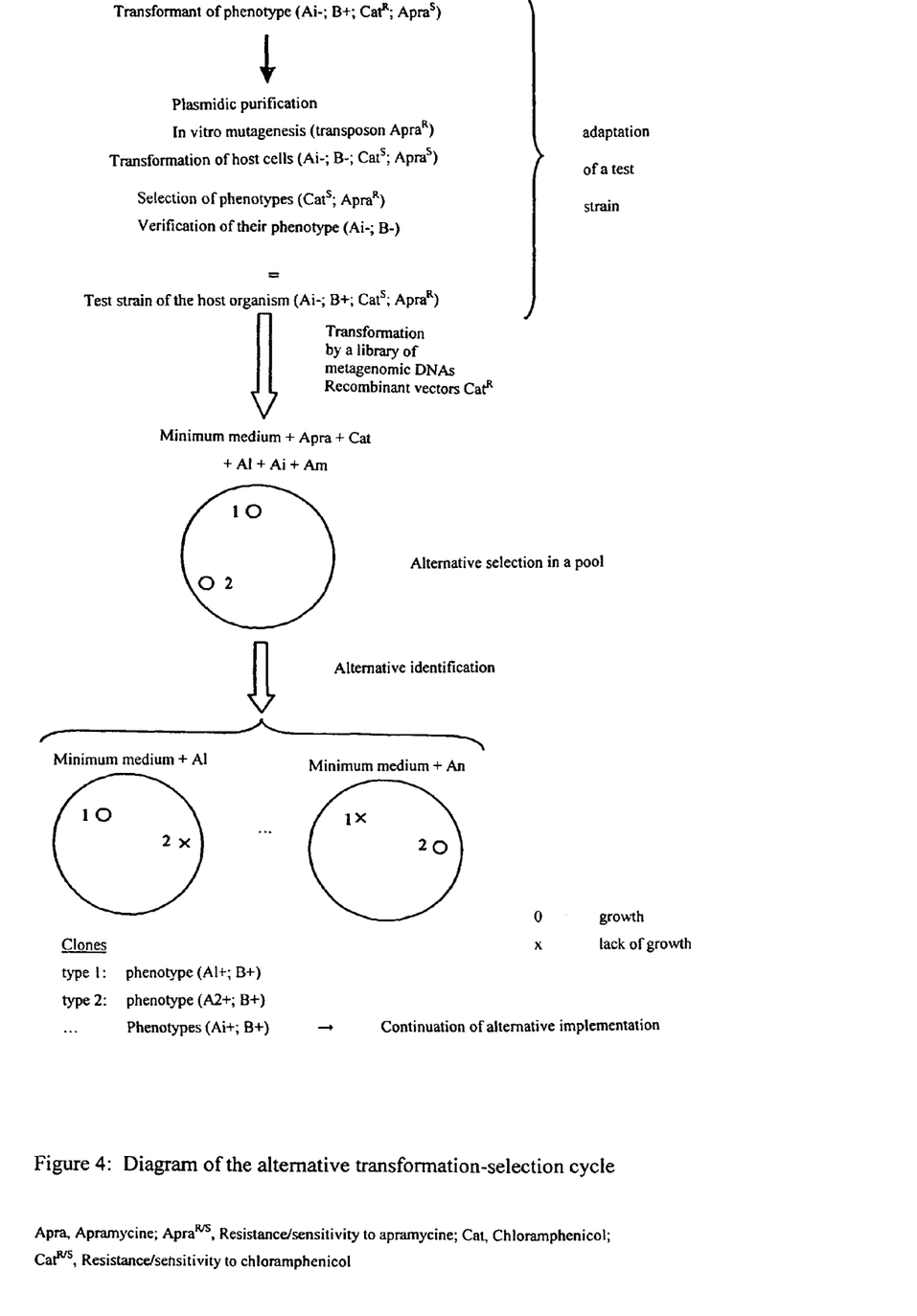
FIG. 4 and FIG. 5: Diagram of the alternative secondary selection cycle.

Step 4: The clones selected on minimum medium containing the n substrates {Ai} and {B} (FIG. 2, clones 1, 2 and 3), are preserved, and then tested in parallel on minimum medium containing either one of the substrates {Ai}, or {B}. For a given substrate {Ai}, this multiple selection makes it possible to identify three distinct phenotypes (FIG. 1):

the phenotype (Ai+; B+) of the clones (of type 1). This corresponds to the desired phenotype preferably corresponding to clones capable of growing on minimum medium with the substrate {Ai} but also with the target product {B} as the only source of an essential element. The clones having this phenotype are preserved and subjected to the following step (FIG. 3).

the phenotype (Ai+; B−) of the clones (of type 2). This corresponds to clones capable of growing on minimum medium with the substrate {Ai} as the only source of an essential element independently of the target product {B}. If they are not processed during the subsequent steps, these clones are nevertheless preserved because they are capable of enriching libraries of enzymes after identification of the metabolic pathways involved in the metabolisation of the substrate {Ai}.

the phenotype (Ai−; B+) of the clones (of type 3). This corresponds to clones incapable of growing on minimum medium with the substrate {Ai} as the only source of an essential element but which are, however, capable of metabolising the target product {B} in order to grow. These clones can advantageously be the object of the development of a receiving strain of the organism, having a phenotype (Ai−; B+), useable in an alternative secondary transformation-selection process of the biocatalysis of {Ai} into {B} (FIG. 4). These clones are also capable of enriching libraries of enzymes after identification of the metabolic pathways involved in the metabolisation of the product {B}.

Step 5: The plasmidic DNA of the recombinant clones of phenotype (Ai+; B+), selected in step 4 and capable of growing both on {Ai} and on {B} is extracted by any of the techniques known by the man skilled in the art (Sambrook et al., 1989 (FIG. 3)). This plasmic DNA is subjected to genetic disruption, advantageously by the random insertion of transposable elements such as those marketed (EZ::TN Epicentre Technologies company) and reintroduced into the host organism (FIG. 3A). The transformants are first of all spread out on rich solid medium until the colonies appear, then the colonies are transferred by replicas onto minimum medium containing just the substrate {Ai} on the one hand, and just the target product {B} on the other hand. The capability of growing on {Ai} and {B} can be the result of a common metabolic pathway (FIG. 3B, genotype [AB]) or of two independent metabolic pathways (FIG. 3B, genotype [A,B]).

Step 6: The parallel selection on {Ai} and {B} of the clones resulting from mutagenesis makes it possible to identify different phenotypes of interest:

the mutated phenotype I (Ai+; B+)* of transposed clones capable of pushing on {Ai} and {B}; either mutagenesis by transposition has no effect in the metagenomic insert or it affects the vector.

the mutated phenotype II (Ai+; B−)* of transposed clones capable of metabolising {Ai} in order to grow but not {B}. The metabolism of {Ai} does not pass via the production of {B} in order to enable growth (FIG. 2, genotype [A,B]).

the mutated phenotype III (Ai−; B−)* of transposed clones capable of using neither {Ai} nor {B} as sources of growth. Either (i) mutagenesis by transposition has reached an element common to the metabolic pathways of {Ai} and {B} such as for example a regulation element, a common transporter; or (ii) the metabolic pathway of {Ai} passes via {B} and the metabolic pathway of {B} enabling growth is disrupted.

Step 7: The passing by {B} into the metabolisation of {Ai} is verified by evaluating the accumulation of {B} by techniques of analytical chemistry when a clone of phenotype (Ai−; B−), isolated in step 4, develops on rich medium.

Step 8: The genetic characterisation of the biocatalyst, i.e. characterisation of the gene or genes encoding the enzyme or enzymes involved in the conversion of {Ai} into {B}, is implemented by means of the transposed clones having the phenotype (Ai−B+). The genetic analysis of the nucleic sequences located on the disruption site or sites of the recombinant clones (Ai−; B+) makes it possible to elucidate the genetic system(s) responsible for the conversion of {Ai} into {B}. The genetic analysis is implemented by any methods known by the man skilled in the art, including non-restrictively establishing sequences of nucleic acids, identifying coding and regulating sequences.

This method makes it possible to gain access rapidly and directly (in a single step) to a metabolic pathway family capable of transforming a substrate {Ai} into a product {B}.

Alternative Transformation-Selection Process

Figure 5:
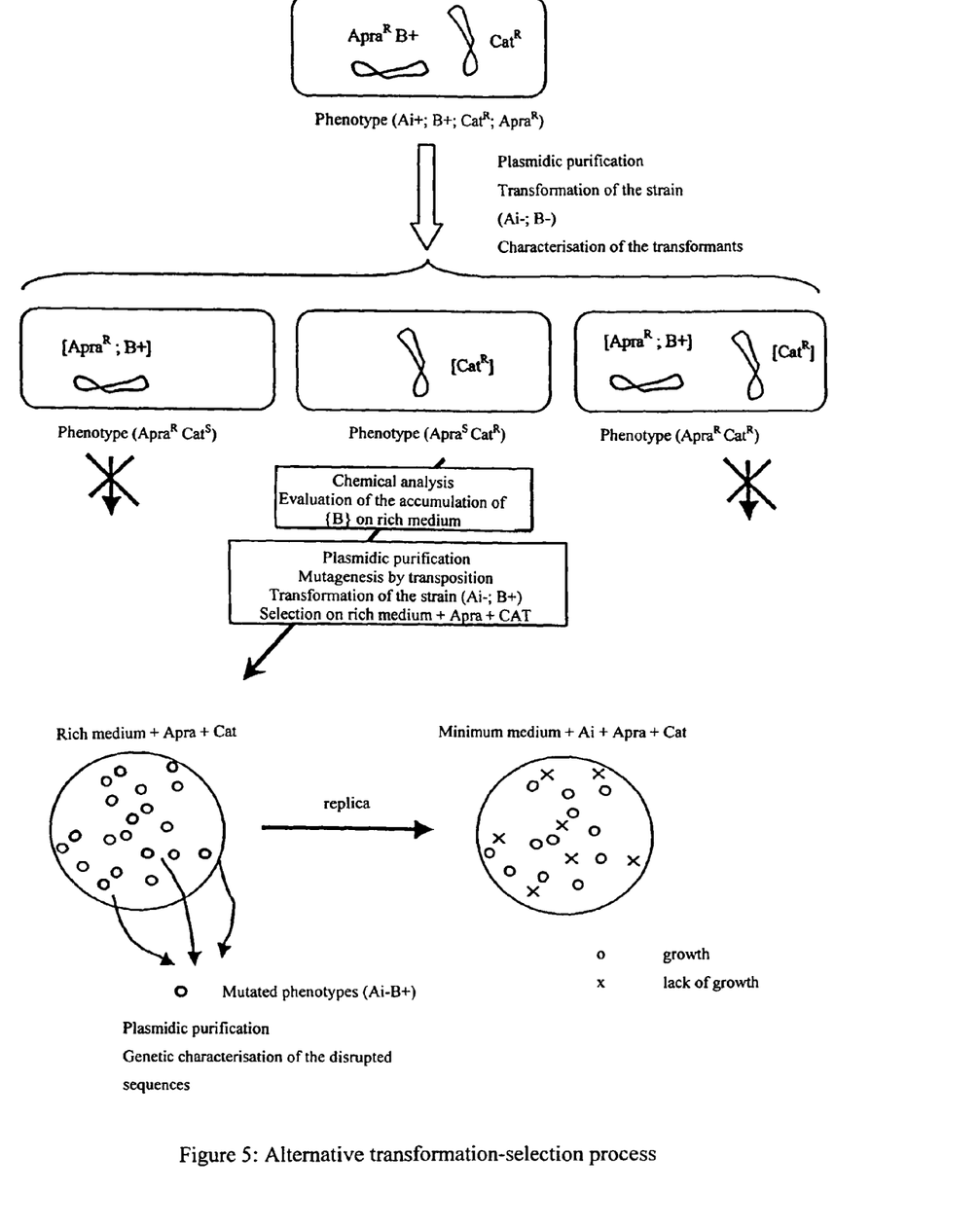

In an alternative embodiment of the invention, in particular when step 4 of the first embodiment does not make it possible to detect clones having a phenotype (Ai+; B+), any phenotypes (Ai−; B+) offer the possibility of developing a receiving strain of phenotype (Ai−; B+) capable of being co-transformed by a second metagenomic library (FIG. 4). This library can be the same as the first library or can be a distinct library. This alternative embodiment makes it possible to exploit, within the metagenomic library, the clones capable of converting at least one of the substrates {Ai} into target product {B} but incapable of metabolising {B} (clones not selected in step 4 of the first embodiment). This alternative embodiment involves several successive steps:

a) Providing a population of transformable host cells (Ai−; B+). This optional step is only necessary if one wishes to transform the population of host cells (Ai−; B+) by a metagenomic or genomic library of DNA selectable by the same resistance marker. This facultative step involves several successive steps (FIG. 4):

plasmidic purification of one or more clones having the phenotype (Ai−; B+), in vitro mutagenesis, advantageously by transposition as described above for step 5 with a transposable element carrying a functional resistance to an antibiotic absent on the target vector (for example resistance to apramycin), on the purified clone or clones, transformation of a population of host cells (Ai−; B−) and selection of the mutations affecting the gene resistant to the antibiotic of the target vector (for example resistance to chloramphenicol). Verification of the growth of this receiving strain on minimum medium with the target product {B} as the only source of carbon makes it possible to rule out the possibility of another mutation event (transposition) altering the function of using {B} for growth. The receiving strain of the organism is then available, capable of growing on apramycin and on minimum medium containing the target product {B} as the only source of an essential element.

b) Transformation of the receiving strain by a metagenomic library of DNA and selection of recombinant clones on minimum medium containing n substrates {Ai} (i between 1 and n) as the only source(s) of an essential element and the two antibiotics of the receiving strain and the recombinant vectors.

c) The clones selected on minimum medium containing the n substrates {Ai} (FIG. 4, clones 1, 2), are preserved, and then tested in parallel on minimum medium containing one of the substrates {Ai}. For a given substrate {Ai}, this multiple selection makes it possible to identify colonies having a phenotype (Ai+; B+) expressing a priori the capability of the clone to grow on the target product {B} by the conversion of the substrate {Ai} into {B}.

d) Plasmidic purification of one or more clone(s) having the phenotype (Ai+; B+). The sample of purified plasmids (FIG. 5) contains in a mixture the recombinant vector Apra$^R$ (metabolic pathway enabling growth on the target product {B}) and the recombinant vector Cat$^R$ (metabolic pathway implementing the conversion of the substrate {Ai} into {B}).

e) The host cell of phenotype (Ai−; B−) is transformed with the mixture of purified recombinant vectors into e) and the recombinant clones Cat$^R$ Apra$^S$ are selected. The conversion of the substrate {Ai} into {B} is verified by evaluating the accumulation of {B} by techniques from analytical chemistry when these clones Cat$^R$ Apra$^S$ develop on rich medium. The accumulation of {B} confirms that these clones Cat$^R$ Apra$^S$ do indeed have a phenotype (Ai+; B−).

f) Plasmidic purification of one or more clone(s) having the phenotype (Cat$^R$ Apra$^S$) identified in f). The recombinant vector is subjected to genetic disruption, advantageously by the random insertion of transposable elements.

g) Transformation of the receiving strain (Ai−; B+) by the population of recombinant vectors mutagenised into g). The transformants are first of all spread over rich solid medium until colonies appear, then the colonies are transferred by replicas on minimum medium containing just the substrate {Ai} as the source of an essential element. The parallel selection of the clones resulting from mutagenesis on rich medium and on minimum medium containing just the substrate {Ai} makes it possible to identify the clones which have become incapable of growing with the substrate {Ai} as the source of an essential element, i.e. in which the disruption affects the metabolic pathway converting {Ai} into {B}.

h) The genetic characterisation of the biocatalyst, i.e. characterisation of the gene or genes encoding the enzyme or enzymes involved in the conversion of {Ai} into {B}, is implemented by means of transposed clones having the phenotype (Ai−; B+). The genetic analysis of the nucleic sequences located on the disruption site or sites of the recombinant clones (Ai−; B+) makes it possible to elucidate the genetic system(s) responsible for the conversion of {Ai} into {B}.

EXAMPLES

Example 1

Search for the Metabolic Pathway for the Bioconversion of Phytosterols into 4-androstene-3,17-dione (AD)

4-androstene-3,17-dione (AD, CAS N° 63-05-8) and 1,4-androstadiene-3,17-dione (ADD, CAS N°897-06-3) are important intermediaries for the pharmaceutical industry, as key precursors for the production of therapeutic steroids. Numerous microorganisms have the natural capability of degrading 3β-hydroxy-Δ5-sterols (for example β-sitosterol, campesterol or brassicasterol) by forming AD and ADD as degradation intermediaries.

The microbic conversion of natural phytosterols into AD by characterised bacterial strains has been widely described (Shashabi B. Mahato et al, 1997 Advances in microbial steroid biotransformation, steroids, 62, 332-345), in particular by *Mycobacterium* sp mutant strains. However, this bioconversion comes up against a number of limitations: the poor solubility of the phytosterols used as substrates, the poor yields associated with significant fermentation times and the concomitant production of AD and ADD which necessitates difficult and costly separation of these two steroid products.

Moreover, scientific studies (van der Geize et al., 2002, Microbiology, 148 :3285-3292) conducted on *Rhodococcus erythropolis* have demonstrated that inactivation of the 3-ketosteroid dehydrogenase (KSTD) enzyme, involved in the catabolism of AD, was not sufficient in order to prevent the growth of *R. erythropolis* on AD, as the only source of carbon and energy.

The aim of the strategy adopted is to detect the metabolic pathways enabling the specific conversion of phytosterols of different AD origin, eliminating the AD catabolic pathways. The metabolic pathways are explored in parallel within a BAC genomic library of *Mycobacterium vaccae* and within a BAC library of metagenomic DNAs originating from soil.

The host organism retained is *Streptomyces lividans*, which meets all of the criteria: cultivatable, transformable bacterium, capable of expressing metabolic pathways originating from *Mycobacterium* and bacteria with a high GC level from soil, known for their capability of degrading phytosterols, and incapable of growing on minimum medium supplemented with phytosterols and androstenedione as the only sources of carbon and energy.

*S. lividans* is transformed by the aforementioned DNA libraries. The transformants are deposited on a solid M9 medium to which is added 10 µg/L of chloramphenicol containing 0.5% phytosterols and 0.5% androstenedione (AD) as the only source of carbon and energy. They are incubated for 5-10 days at 30° C. The clones retained which are capable of growing are then tested separately on minimum medium supplemented with phytosterols on the one hand and AD on the other hand. The capability of growing on phytosterols and/or on AD is linked to the DNAs introduced during the transformation.

The clones capable of growing both on phytosterols and on AD as the only sources of carbon are selected, their vectors are re-extracted and then subjected to in vitro mutagenesis by transposition (EZ:TN Epicentre Technologies transposition kit). The mutated recombinant vectors are re-introduced into *S. lividans*. The transformants are deposited on rich medium and are tested in parallel on a solid M9 medium to which is added 10 µg/L of chloramphenicol containing 0.5% phytosterols on the one hand, and 0.5% androstenedione (AD) on the other hand, as the only source of carbon and energy. The *S. lividans* clones having lost the capability of growing on phytosterols but capable of growing on AD are selected, and their recombinant vector re-extracted. The genetic characterisation of metabolic pathways involved in the conversion of the phytosterols into AD is implemented by sequencing said recombinant vectors previously selected.

Example 2

Search for the Metabolic Pathway for the Bioconversion of 1-phenyl-2-propanone into 1-phenyl-2-propanol Phenyl-2-propanol (CAS N N°103-79-7) is a compound widely used as a structural motif making up numerous active principles (Liese, A. et al, 2000, Industrial Biotransformation ed Wiley-VCH 103-106). It is found in particular as an intermediary for the synthesis of amphetamines (Bracher, F. et al, 1994, Arch. Pharm. 327, 591-593). Bacteria such as *Rhodococcus erythropolis* (Liese, A. et al 2000), but also the yeast *Saccharomyces Cerevisiae* (Gillois, J. et al, 1989, Journal of Organometallic Chemistry 367(1-2), 85-93) have been described in order to catalyse the reaction A shown below, but with reactional yields of around 70%.

Reaction A: Bioconversion of 1-phenyl-2-propanone into 1-phenyl-2-propanol.

1-phenyl-2-propanone → 1-phenyl-2-propanol

The following strategy is adopted in order to select a novel and very effective metabolic pathway family which catalyses the bioconversion of 1-phenyl-2-propanone into 1-phenyl-2-propanol (CAS N° 698-87-3).

The culture media are sterilised in the autoclave at 121° C. for 20 minutes. Casamino acid, L-Tryptophane and Thiamine HCl are cold sterilised using a 0.2 μm millipore membrane and are added to the culture medium following sterilisation. 1-phenyl-2-propanone and 1-phenyl-2-propanol are dissolved in ethanol and cold sterilised, then filtered using a 0.2 μm millipore membrane before being incorporated into the gelose.

The *E. Coli* DH10B (LifeTechnologies, Gibco BRL) host strain is previously spread over a solid M9 medium (composition for 1 liter: 6.0 g $Na_2HPO_4$; 3.0 g $KH_2PO_4$; 1.0 g NaCl; 2.0 g glucose; 0.25 g $MgSO_4$, $7H_2O$; 15.0 mg $CaCl_2$, $2H_2O$; 5.0 g Casamino acids; 40.0 mg L-Tryptophane; 1.0 mg Thiamine HCl; distilled water qsp) containing 0.5% (V/V) 1-phenyl-2-propanone (Aldrich ref 13,538-0, CAS 103-79-7) or 1-phenyl-2-propanol (Aldrich ref 14,923-5, CAS 14898-87-4) as the only source of carbon and energy. The Petri dishes are left to incubate for 18-24 hrs at 30° C. No clones should appear under these conditions, demonstrating that the *E. Coli* DH10B strain is incapable of catabolising 1-phenyl-2-propanone or 1-phenyl-2-propanol.

This strain is then transformed by the libraries of environmental DNA prepared and produced according to the operating conditions described in patents WO 01/81367 and EP N°02291871.8. The transformants are deposited on a solid M9 medium to which is added 10 μg/L of chloramphenicol (cold sterilised, as described above) containing 0.5% 1-phenyl-2-propanone or 1-phenyl-2-propanol as the only source of carbon and energy. They are incubated for 18-24 hrs at 30° C. The clones retained are those which are capable of growth with, as the only source of carbon and energy, 1-phenyl-2-propanone and 1-phenyl-2-propanol. The possibility of using these 2 compounds as the only source of carbon and energy is linked to the metagenomic DNA carried by the cloning vectors.

The vectors which carry the metagenomic DNAs in question are obtained and then subjected to random mutagenesis, for example by insertion (transposon kit Epicentre Technologies EZ: TN). They are then re-introduced into the *E. Coli* DH10B strain and the cells transformed in this way are once again deposited onto a solid M9 medium to which is added 10 μg/L chloramphenicol and containing 0.5% 1-phenyl-2-propanone or 1-phenyl-2-propanol as the only source of carbon and energy. They are incubated for 18-24 hrs at 30° C.

The clones retained are those which prove to be incapable of growth with 1-phenyl-2-propanol and 1-phenyl-2-propanone as the only source of carbon. In fact, the pathway for the bioconversion of 1-phenyl-2-propanone into 1-phenyl-2-propanol is present in these clones, and the mutation has deactivated this pathway. A chromatographic analysis using liquid or gaseous Chromatography makes it possible both to verify this transformation and to exclude any false positives.

Example 3

Search for the Metabolic Pathway for the Bioconversion of Mandelonitrile into Mandelic Acid and of Mandelonitrile into Mandelamide The study of the microbiological hydrolysis of nitriles into carboxylic acid or into amide has been described in great detail (Wieser, M. et al (2000), Stereoselective biocatalysis Ed Patel RN "Stereoselective nitrile-converting enzymes"; Ryuno, K. et al (2003), Yuki Gosei Kagaku Kyokaishi 61(5), 517-522; Okumura, M. (1991), JETI 39(6), 90-2; Endo, R., et al (2001), Jpn. Kokai Tokkyo Koho, Application: JP 2000-124591 20000425).

Patent EP-A-0 348 901 describes the preparation of R(−)-mandelic acids by hydrolysis of racemic mandelonitrile by a preparation either of *Alcaligenes fecalis*, ATCC 8750 strain, or of *Pseudomonas vesicularis*, ATCC 11426 strain, or of *Candida tropicalis*, ATCC 20311 strain. It proposes producing optically active α-substituted carboxylic acids from nitriles or from racemic a-substituted amides with the help of certain microorganisms from the group made up of the *Alcaligenes*, *Pseudomonas*, *Rhodopseudomonas*, *Corynebacterium*, *Acinetobacter*, *Bacillus*, *Mycobacterium* and *Rhodococcus* genuses as well as a yeast, namely *Candida*.

In patent EP-A-449 648 or U.S. Pat. No. 5,296,373, a process is described for producing the acid enantiomer, R(−)-mandelic substituted from a racemic substituted mandelonitrile by mixing with a preparation of a *Rhodococcus* bacterium, HT 29-7 (FERM BP-3857) strain which guarantees the stereoselective hydrolysis of the nitrile group of the racemic in order to, apparently, avoid the disadvantages of the separation of other optically active substances obtained after hydrolysis by the microorganisms proposed in EP-A-0 348 901. Patent EP-A-0 610 048 proposes using, in a similar reaction, microorganisms of the *Gordona* genus, such as *Gordona terrae* MA-1 (FERM BP-4535).

One of the main problems encountered with these reactions is the appearance of numerous sub-products (aldehydes) and the short half-life duration of the enzyme due to the poisoning of the catalyst by the nitriles. The object of this example proposes producing from mandelonitrile either chiral mandelic acid (Reaction B), or mandelamide (Reaction C) without the problems generally encountered and with strong specific activity and a high reactional yield.

Reaction B: Bioconversion of mandelonitrile into mandelic acid

Reaction C: Bioconversion of mandelonitrile into mandelamide

The strategy used is identical to that adopted in example 1, simply with substitution of the starting substrates and the products arrived at. Mandelonitrile (CAS N°532-28-5), mandelic acid (CAS N°90-64-2) and mandelamide (CAS N°4410-31-5) are placed in solution in acetonitrile and prepared extemporaneously before being used.

The metabolic pathways catalysing the desired reaction are confirmed by a liquid chromatography analysis.

The invention claimed is:

1. A method for selecting cells comprising at least one metabolic pathway or metabolic pathway family enabling the transformation of a substrate {Ai} into a desired product {B}, comprising the following steps:
   a) providing a population of host cells (Ai−; B−) incapable of metabolizing said substrate {Ai} and said product {B};
   b) transforming said population of host cells with a metagenomic library of nucleic acid sequences;
   c) testing the ability of said population of transformed host cells to grow on a minimum medium containing said substrate {Ai} selected from the group consisting of phytosterols, 1-phenyl-2-propanol and mandelonitrile as the only source of an element essential to growth and testing the ability of said population of transformed host cells to grow on another minimum medium containing said product {B} as the only source of an element essential to growth; and
   d) selecting said host cell(s) capable of growth on the minimum medium containing substrate {Ai} and on the minimum medium containing said product {B} so that the host cell(s) having a phenotype (Ai+; B+) is selected, and wherein host cell(s) having the phenotype (Ai+; B+) comprises metabolic pathway or metabolic pathway family enabling the transformation of at least one substrate {Ai} into the desired product [B], and wherein i is a whole number between 1 and 100.

2. The method according to claim 1, comprising, before step c), a step consisting of testing said population of transformed host cells on a minimum medium containing the substrate(s) {Ai} and said product {B} as the only source of an element essential to growth and selecting said host cell(s) capable of growth on said minimum medium containing the substrate(s) {Ai} and said product {B}; said selected host cell(s) then being subjected to step c) and the subsequent steps.

3. The method according to claim 1, comprising, after step c), in parallel to step d) and the subsequent steps, the following steps:
   k) selecting said transformed host cell(s), incapable of growth on a minimum medium containing one of the substrates {Ai} and capable of growth on a minimum medium containing said product {B}, called receiving cell(s) (Ai−; B+);
   l) transforming said receiving cell(s) (Ai−; B+) with a metagenomic library of sequences of nucleic acid;
   m) testing in parallel said transformed receiving cell(s) (Ai−; B+) on a minimum medium containing one of the substrate(s) {Ai};
   n) selecting said transformed receiving cell(s) capable of growth on a minimum medium containing one of the substrates {Ai}; and
   o) characterizing the nucleic acid encoding an enzyme or enzymes involved in the conversion of the substrate {Ai} into product {B} in said transformed receiving cell(s) (Ai+; B+) selected in step n).

4. The method according to claim 1, in which said metagenomic library nucleic acid sequences originates from cultivatable prokaryotic or eukaryotic organisms.

5. The method according to claim 1, in which said metagenomic library of nucleic acid sequences originates from non-cultivatable prokaryotic or eukaryotic organisms.

6. The method according to claim 4, wherein said cultivatable prokaryotic organism is a bacterium.

7. The method according to claim 5, wherein said non-cultivatable prokaryotic organism is a bacterium.

8. The method according to claim 1, wherein said host cell is *Streptomyces lividans*.

* * * * *

UNITED STATES PATENT AND TRADEMARK OFFICE
CERTIFICATE OF CORRECTION

| | | |
|---|---|---|
| PATENT NO. | : 7,846,874 B2 | |
| APPLICATION NO. | : 10/591087 | |
| DATED | : December 7, 2010 | |
| INVENTOR(S) | : Pierre Monsan et al. | |

It is certified that error appears in the above-identified patent and that said Letters Patent is hereby corrected as shown below:

Column 13,
Line 2, "K. Struhi" should read --K. Struhl--.

Column 14,
Lines 63-64, "of {B} enabling growth is disrupted.
    Step 7 : The passing by {B} into the metabolisation of {Ai}"
should read --of {B} enabling growth is disrupted.
       the mutated phenotype IV (Ai- ; B+)* of transposed clones capable of using
        {B} but not {Ai} in order to grow. The metabolic pathway in question
        enabling the conversion of the substrate {Ai} into the target product {B}
        is disrupted.
    Step 7 : The passing by {B} into the metabolisation of {Ai}--.

Column 22,
Line 6, "comprises metabolic" should read --comprises at least one metabolic--.
Lines 7-8, "of at least one substrate {Ai}" should read --of substrate {Ai}--.
Line 8, "desired product [B}" should read --desired product {B}--.

Signed and Sealed this
Twenty-second Day of February, 2011

David J. Kappos
*Director of the United States Patent and Trademark Office*